United States Patent [19]
Bradshaw et al.

[11] Patent Number: 5,662,580
[45] Date of Patent: *Sep. 2, 1997

[54] COMBINED ANGIOPLASTY AND INTRAVASCULAR RADIOTHERAPY METHOD AND APPARATUS

[75] Inventors: Anthony J. Bradshaw, Missouri City; Richard T. Thornton, League City; Wayne W. Snyder, Houston, all of Tex.

[73] Assignee: NeoCardia, LLC, Houston, Tex.

[ * ] Notice: The term of this patent shall not extend beyond the expiration date of Pat. No. 5,616,114.

[21] Appl. No.: 386,419

[22] Filed: Feb. 10, 1995

Related U.S. Application Data

[63] Continuation-in-part of Ser. No. 352,318, Dec. 8, 1994.
[51] Int. Cl.$^6$ .................................................. A61N 5/00
[52] U.S. Cl. .................................................. 600/3
[58] Field of Search .................. 600/1–8; 606/7, 606/108, 192, 194, 198

[56] References Cited

U.S. PATENT DOCUMENTS

| | | | |
|---|---|---|---|
| 3,324,847 | 6/1967 | Zoumboulis . | |
| 4,250,887 | 2/1981 | Dardik et al. | 128/655 |
| 4,471,765 | 9/1984 | Strauss et al. | 600/5 |
| 4,601,713 | 7/1986 | Fuqua | 604/280 |
| 5,059,166 | 10/1991 | Fischell et al. . | |
| 5,106,360 | 4/1992 | Ishiwara et al. | 600/2 |
| 5,199,939 | 4/1993 | Dake et al. | 600/3 |
| 5,302,168 | 4/1994 | Hess . | |
| 5,334,154 | 8/1994 | Samson et al. | 604/102 |

FOREIGN PATENT DOCUMENTS

| | | | |
|---|---|---|---|
| 9102312 U | 8/1992 | Germany . | |
| 793158 | 12/1956 | United Kingdom | 600/3 |

OTHER PUBLICATIONS

Böttcher, H.D., et al., *Endovascular Irradiation—A New Method to Avoid Recurrent Stenosis After Stent Implantation in Peripheral Arteries: Technique and Preliminary Results;* Nov. 1992; pp. 183–186.

*Primary Examiner*—Angela D. Sykes
*Assistant Examiner*—Samuel Gilbert
*Attorney, Agent, or Firm*—Wigman, Cohen, Leitner & Myers, P.C.

[57] ABSTRACT

Apparatus and methods are provided for relieving a stenosed region of a blood vessel such as a coronary using a single catheter that relieves the angioplasty by conventional means and then delivers an easily controllable inherently uniform dosage of radiation to the walls of a blood vessel for preventing restenosis after angioplasty. An embodiment of the apparatus comprises a catheter having an angioplasty balloon that is inflatable with a liquid containing a suspended radioactive material such as $^{125}$I or $^{32}$P. The balloon is surrounded by a membrane to capture the radioactive liquid in the event the balloon ruptures. The catheter is advanced through the patient until the balloon is disposed in the stenosed region of the blood vessel. The stenosed region is relieved using the angioplasty balloon, after which the angioplasty balloon is emptied and re-filled with the radioactive liquid, which expands the balloon to engage the walls of the blood vessel thereby providing an inherently uniform dosage of radiation to the blood vessel walls.

Another embodiment of the apparatus comprises a catheter having an angioplasty balloon surrounded by a radiotherapy treatment balloon that is separately inflatable with a radioactive liquid. The stenosed region is relieved using the inner angioplasty balloon after which the radiotherapy treatment balloon is filled with the radioactive liquid. An additional containment balloon outside the radiotherapy treatment balloon may also be provided to prevent loss of radioactive liquid in the event the treatment balloon ruptures. The angioplasty balloon may be partly filled during the radiation treatment to minimize the volume of radioactive liquid necessary to achieve the desired dosage.

22 Claims, 4 Drawing Sheets

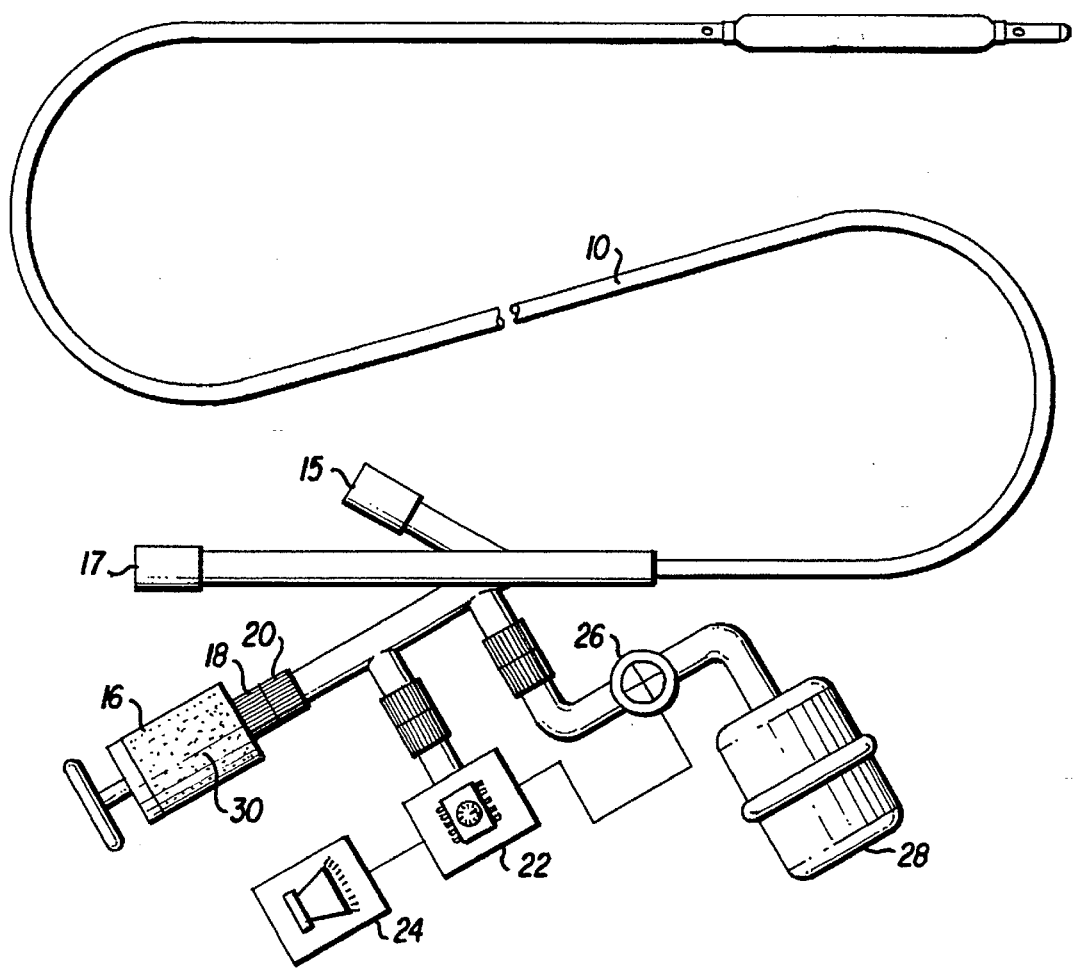
FIG. 1A
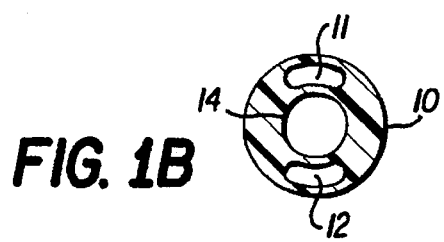
FIG. 1B
FIG. 1C
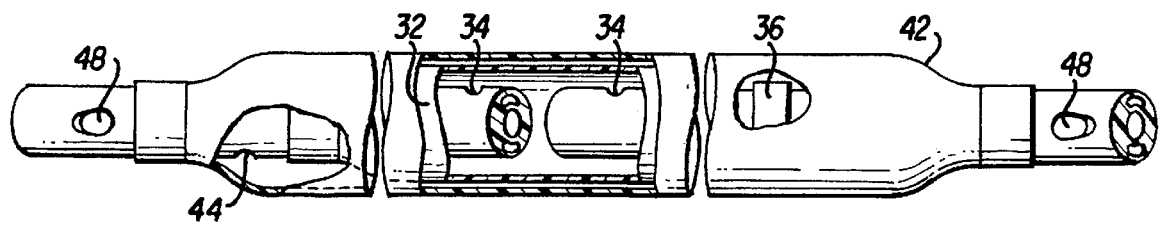

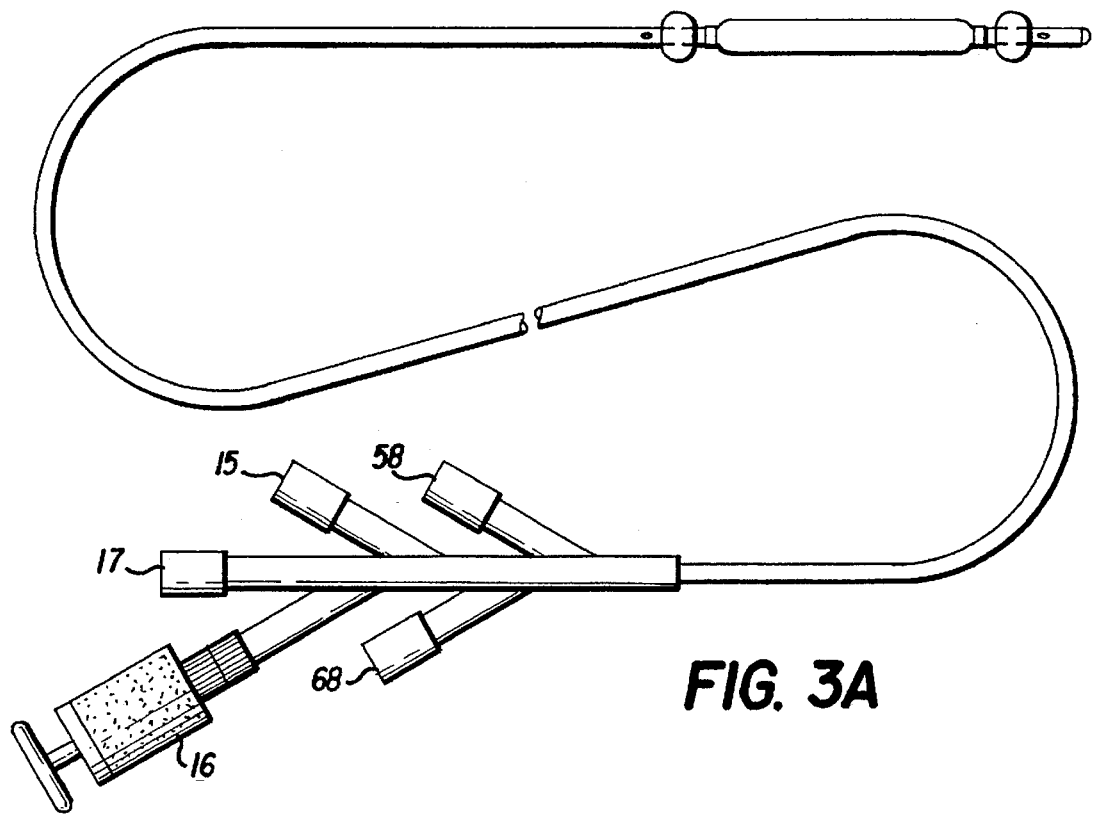
FIG. 3A
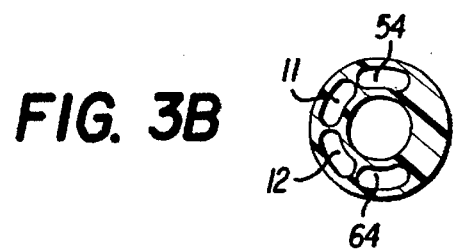
FIG. 3B
FIG. 3C
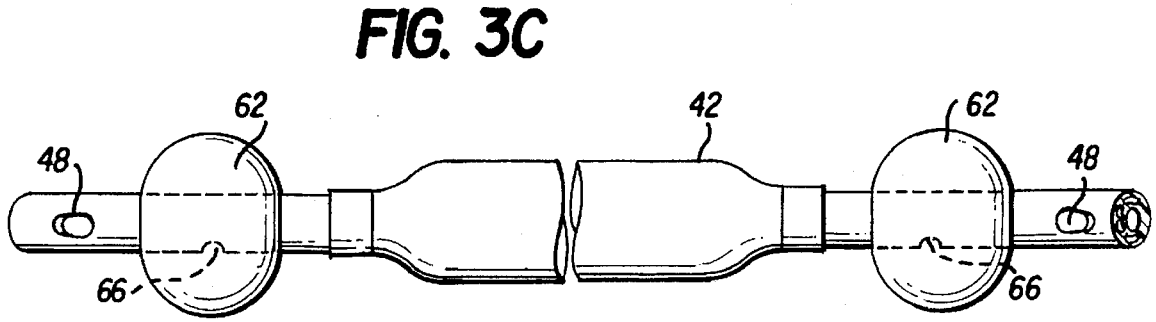

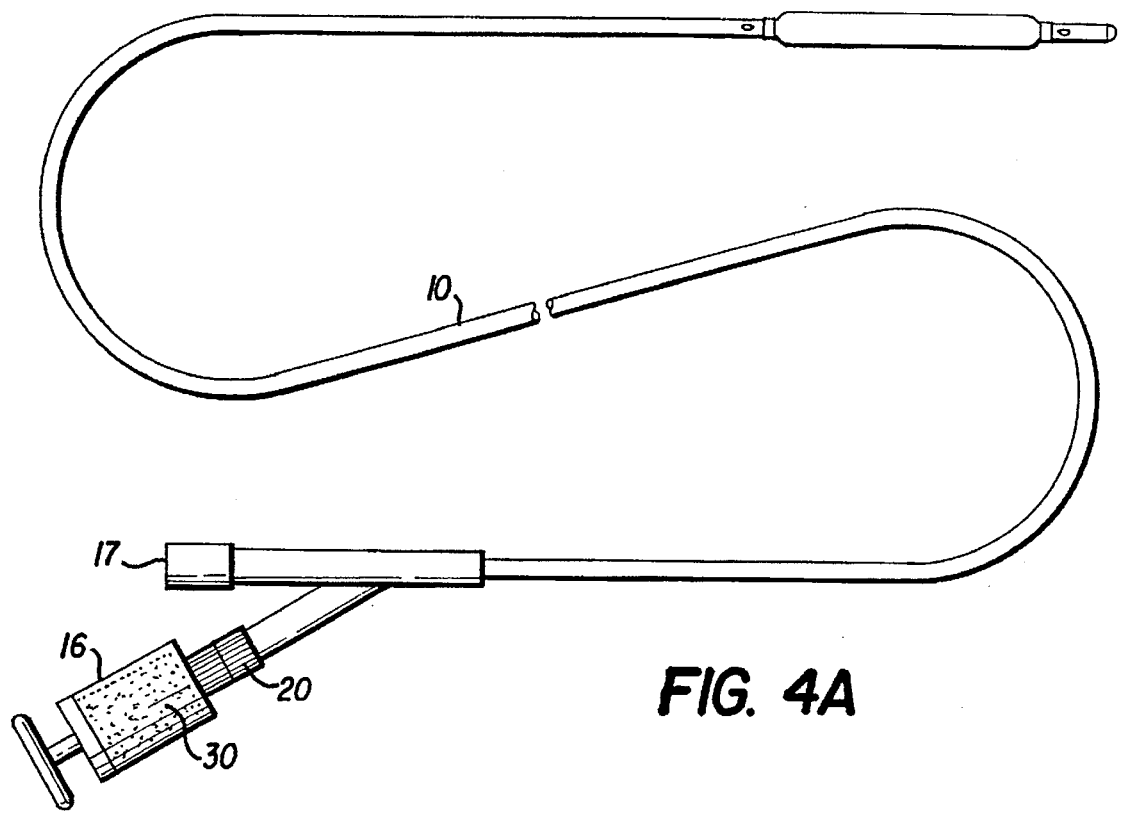
FIG. 4A
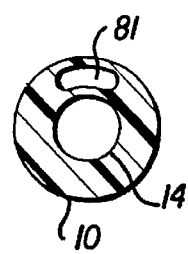
FIG. 4B
FIG. 4C
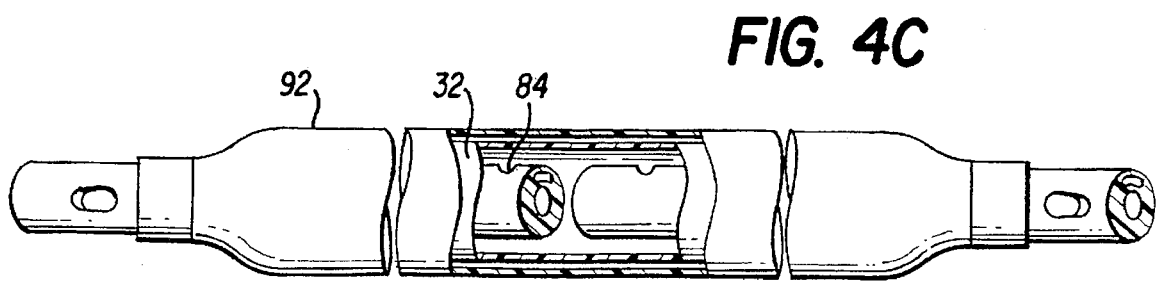

COMBINED ANGIOPLASTY AND INTRAVASCULAR RADIOTHERAPY METHOD AND APPARATUS

CROSS-REFERENCE TO RELATED APPLICATION

This application is a continuation-in-part of co-pending U.S. application Ser. No. 08/352,318 filed Dec. 8, 1994.

BACKGROUND OF THE INVENTION

This invention relates generally to treatment of selected tissue by inter-vivo radiation, specifically to radiation treatment of traumatized regions of the cardiovascular system to prevent restenosis of the traumatized region, more specifically to radiation treatment to prevent restenosis of an artery traumatized by percutaneous transluminal angioplasty (PTA).

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States (U.S.) in 1990 and an estimated 400,000 in 1992. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% of all patients requiring repeat PTCA procedures or by-pass surgery, with attendant high cost and added patient risk. More recent attempts to prevent restenosis by use of drugs, mechanical devices, and other experimental procedures have had limited success.

Restenosis occurs as a result of injury to the arterial wall during the lumen opening angioplasty procedure. In some patients, the injury initiates a repair response that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Preliminary studies indicate that intravascular radiotherapy (IRT) has promise in the prevention or long-term control of restenosis following angioplasty. It is also speculated that IRT may be used to prevent stenosis following cardiovascular graft procedures or other trauma to the vessel wall. Proper control of the radiation dosage, however, is critical to impair or arrest hyperplasia without causing excessive damage to healthy tissue. Overdosing of a section of blood vessel can cause arterial necrosis, inflammation and hemorrhaging. Underdosing will result in no inhibition of smooth muscle cell hyperplasia, or even exacerbation of the hyperplasia and resulting restenosis.

U.S. Pat. No. 5,059,166 to Fischell discloses an IRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. Additionally, the dose delivered to the blood vessel is non-uniform because the tissue that is in contact with the individual strands of the stent receive a higher dosage than the tissue between the individual strands. This non-uniform dose distribution is especially critical if the stent incorporates a low penetration source such as a beta emitter.

U.S. Pat. No. 5,302,168 to Hess teaches use of a radioactive source contained in a flexible carrier with remotely manipulated windows. H. Böttcher, et al. of the Johann Wolfgang Goerhe University Medical Center, Frankfurt, Germany report in November 1992 of having treated human superficial femoral arteries with a similar endoluminal radiation source. These methods generally require use of a higher activity source than the radioactive stent to deliver an effective dose. Accordingly, measures must be taken to ensure that the source is maintained reasonably near the center of the lumen to prevent localized overexposure of tissue to the radiation source. Use of these higher activity sources also dictates use of expensive shielding and other equipment for safe handling of the source.

The aforementioned application Ser. No. 08/352,318, incorporated herein by reference, discloses IRT methods and apparatus for delivering an easily controllable uniform dosage of radiation to the walls of the blood vessel without the need for special measures to center the radiation source in the lumen, the need for expensive shielding to protect medical personnel, or the need for expensive remote afterloaders to handle the higher activity sources. This is accomplished by introducing a radioactive liquid into a balloon catheter to expand the balloon until it engages the blood vessel walls. The aforementioned application also discloses methods and apparatus for relieving the stenosed region of the blood vessel and performing the IRT procedure with a single apparatus, which may include an angioplasty balloon with a separately inflatable outer IRT balloon.

In certain applications, however, the size of the blood vessel is too small to admit a catheter with a profile large enough to accommodate separate inflation lumens for an outer and inner balloon. A smaller profile IRT catheter be obtained, however, by eliminating the IRT inflation lumen, thereby converting the outer IRT balloon to a containment membrane.

Where the blood vessel size permits, a further advantage may be obtained, if a combination angioplasty and IRT catheter includes means for extending the IRT treatment area beyond the angioplasty treatment area to irradiate a region extending proximal and distal of the angioplasty treatment area. By providing for IRT treatment that covers a wider area than the angioplasty treatment area, all of the tissue traumatized by the angioplasty is irradiated with the measured dosage, even if the catheter is displaced between the angioplasty and IRT procedures. Accordingly, proper inhibition of smooth muscle cell hyperplasia is more reliably achieved.

SUMMARY OF THE INVENTION

According to the present invention, a single treatment catheter is used to perform all, or at least the final stage, of the angioplasty procedure and to perform the entire IRT procedure. In an embodiment of the present invention, the treatment catheter comprises a flexible elongate member having an angioplasty balloon that is surrounded by an IRT treatment balloon having a separate inflation lumen. The catheter is advanced through the cardiovascular system of the patient until the balloons are positioned at a targa area comprising the stenosed region of the blood vessel. The stenosis is first relieved using the inner angioplasty balloon, then the target tissue is irradiated by filling the IRT treatment balloon with a radioactive liquid until the outer wall of the balloon gently engages the inner wall of the blood vessel.

The radioactive liquid comprises a suspension of a beta emitting material such as $^{32}P$ or a photon emitting material such as $^{125}I$ in a liquid carrier. The radiation emitted by such sources is quickly absorbed by surrounding tissue and will not penetrate substantially beyond the walls of the blood vessel being treated. Accordingly, incidental irradiation of the heart and other organs adjacent to the treatment site is substantially eliminated. Because the radioactive liquid has a substantially uniform suspension of radioactive material, the radiation emitted at the surface of the balloon in contact with the target area of the blood vessel is inherently uniform. Accordingly, uniform irradiation of the blood vessel wall is also inherent.

According to an embodiment of the present invention, the outer IRT treatment balloon is made longer than the inner angioplasty balloon. Accordingly, when filled, the IRT treatment balloon will irradiate a section of the blood vessel that extends on both sides beyond the area treated with the angioplasty balloon. This extended IRT treatment area provides a margin of safety to ensure that, even if the catheter shifts slightly during the treatment, the entire traumatized region of the blood vessel will be treated to prevent smooth muscle cell hyperplasia.

The catheter of the present invention may also be equipped with perfusion ports proximal and distal of the balloon to permit blood flow past the balloon when inflated.

According to another embodiment of the present invention, a third balloon is provided that completely envelopes the IRT treatment balloon. This containment balloon acts as a containment vessel in the event the IRT treatment balloon ruptures when filled with the radioactive liquid. In use, prior to filling the treatment balloon with the radioactive liquid, the containment balloon is filled, preferably with a non-toxic radio-opaque fluid, to verify the integrity of the containment balloon. The radio-opaque fluid filled containment balloon may also be used to verify correct positioning of the catheter within the target area of the blood vessel.

After the angioplasty procedure is performed, the angioplasty balloon may be deflated, or left partially inflated. Leaving the angioplasty balloon partially inflated reduces the amount of radioactive liquid that must be used to fill the treatment balloon by occupying space within the IRT treatment balloon. Because of the self-attenuation of the radioactive liquid itself, most of the radioactivity originates at the surface of the treatment balloon. Accordingly, the surface radiation is not reduced substantially as a result of the center being filled with an inert material.

According to another embodiment of the present invention, a proximal and distal blocking balloon are also provided to contain the radioactive liquid in the target area in the event of a total failure of all containment systems.

According to another embodiment of the present invention, where a very low profile is required to access small blood vessels, the catheter comprises an inner angioplasty balloon and an outer balloon, however, the outer balloon inflation lumen is eliminated, thereby converting the outer balloon to a containment membrane. The IRT procedure is then carried out by filling the angioplasty balloon itself with the radioactive liquid after the angioplasty procedure has been performed. The containment membrane contains the radioactive liquid in the unlikely event that the angioplasty balloon, which previously withstood angioplasty pressures, ruptures under the more moderate IRT pressure.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which:

FIGS. 1A–1C are plan and cross sectional views of an apparatus according to the present invention;

FIGS. 3A–3C are plan and cross sectional views of an alternate embodiment of an apparatus according to the present invention incorporating proximal and distal blocking balloons.

FIGS. 4A–4C are plan and cross sectional views of an alternate embodiment of an apparatus according to the present invention comprising a low profile catheter with a containment membrane.

DESCRIPTION OF PREFERRED EMBODIMENTS AND METHODS

Figure 2A:
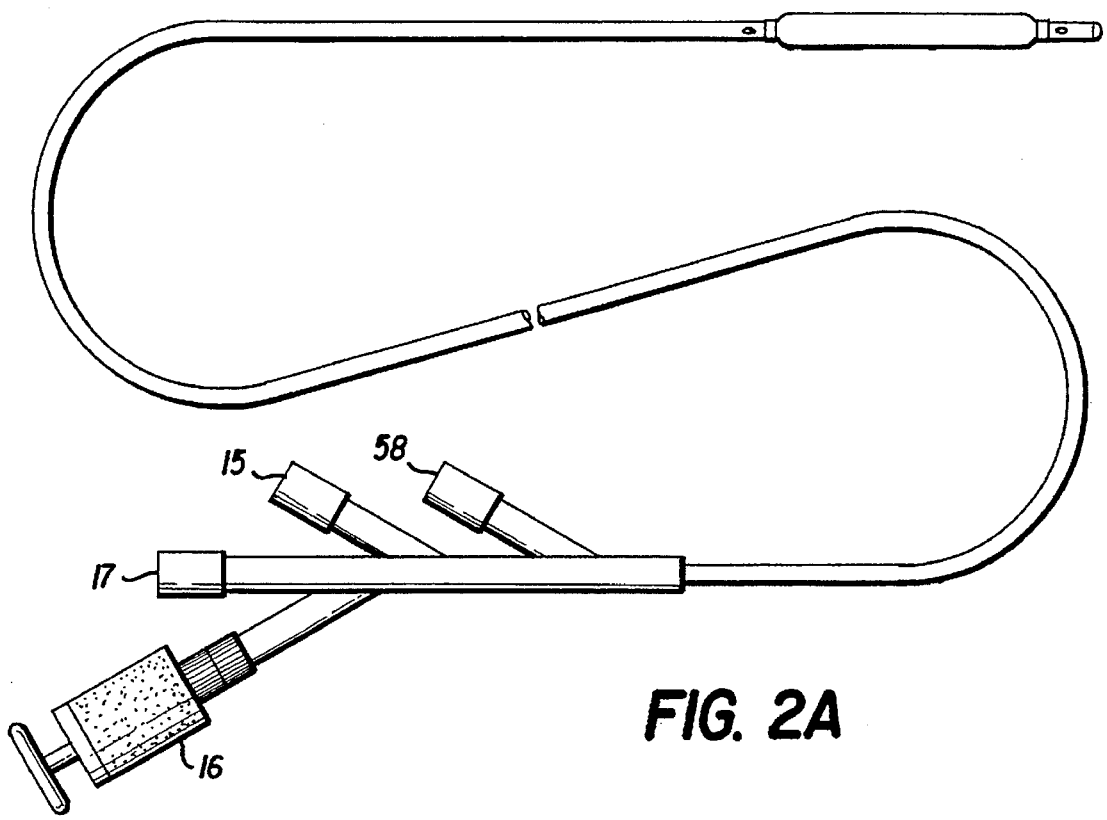
FIGS. 2A–2C are plan and cross sectional views of an alternate embodiment of an apparatus according to the present invention incorporating a containment balloon.

FIGS. 1A and 1B illustrate a suspended-isotope IRT catheter according to the present invention. The IRT catheter comprises shaft 10 having an angioplasty inflation lumen 11, IRT inflation lumen 12, a conventionally formed tip that seals the end of the inflation lumens, and may include longitudinal guidewire/injection/perfusion lumen 14 which passes through the tip. Shielded injector 16, which may be a manual or automated syringe containing a radioactive liquid 30, or a pump connected to a reservoir of radioactive liquid 30, is connected to the proximal end of shaft 10 and is in fluid communication with IRT inflation lumen 12. To prevent possible spillage and corresponding radioactive contamination of the operating room and/or its personnel, the shielded injector 16 is permanently attached to shaft 10, or preferably, injector 16 is equipped with a fail-safe non-detachable connector 18, which cannot be detached from the corresponding receptacle 20 of shaft 10 once it is attached thereto. Non-detachable connector 18 also prevents the radioactive liquid 30 from being discharged from injector 16 until the connector is connected to the receptacle in shaft 10. Connectors having ring-detents and other non-detachable fluid fittings are well known in the art, as are piercing valves and other common methods of preventing fluid flow prior to attachment of a fluid fitting. The proximal end of shaft 10 also includes angioplasty luer fitting 15 in fluid communication with angioplasty inflation lumen 11, and guidewire lumen luer fitting 17 in fluid communication with guidewire lumen 14, through which drugs may be injected directly into the patient's blood stream.

FIG. 1C is an enlarged view of the distal end of the present embodiment of the catheter. Angioplasty balloon 32 comprises a conventional elastic or preferably an inelastic balloon, which may preferably be made from polyethylene terephthalate (PET), polyvinyl chloride (PVC), or other medical grade material suitable for constructing a strong non-compliant balloon. Angioplasty balloon 32 is in fluid communication with angioplasty inflation lumen 11 via ports 34. Immediately inside proximal and distal ends of balloon 32 are markers 36, comprising bands of silver or other suitable x-ray opaque material. Markers 36 aid in the proper positioning of angioplasty balloon 32 within the target area of the blood vessel under fluoroscopy.

IRT Treatment balloon 42 is disposed at the distal end of shaft 10 surrounding angioplasty balloon 32. IRT treatment balloon is an elastic or preferably an inelastic balloon, which may preferably be made from polyethylene terephthalate (PET), polyvinyl chloride (PVC), or other medical grade material suitable for constructing a strong non-compliant balloon. IRT treatment balloon 42 is sealed at its proximal and distal ends to catheter shaft 10 in fluid communication with inflation lumen 12 via inflation lumen ports 44.

Immediately adjacent to and outside the ends of IRT treatment balloon 42 are perfusion ports 48, which are in fluid communication with guidewire lumen 14. Perfusion ports are well known in the art as a means of permitting some blood flow past a balloon that is inflated within and otherwise blocking a blood vessel.

In operation, an appropriately sized catheter according to the present invention is selected and positioned within the patient's blood vessel by conventional means so that the balloon is within the target area comprising the stenosed region of the blood vessel. The stenosis is relieved by inflating the angioplasty balloon according to conventional methods. After the angioplasty procedure has been performed, shielded injector 16 is connected to the receptacle at the proximal end of the catheter shaft and the air evacuated from the IRT treatment balloon and the inflation lumen. In the case of a shielded syringe, this is done simply by withdrawing the plunger. The balloon is then filled with the liquid containing the suspended isotope until the outer wall of the balloon gently engages the inner wall of the blood vessel. The balloon is maintained in this inflated state for a predetermined period of time calculated to deliver an effective dose of radiation to the wall of the blood vessel. The radioactive liquid is then withdrawn from the balloon and the catheter withdrawn from the patient's body.

To reduce the chances of overpressurizing the treatment balloon and causing a rupture, pressure feedback device 22 is connected to the proximal end of inflation lumen 12. Pressure feedback device 22 may be a pressure gauge, or preferably a solid-state pressure transducer, which in the in the event an overpressure condition is detected, operates an alarm 24 and/or a waste gate 26 that discharges the inflation lumen 12 into a shielded container. Alternately, the solid state pressure transducer may be positioned at the distal end of the inflation lumen to monitor pressure in the balloon directly.

For added safety, prior to filling IRT treatment balloon with radioactive liquid, IRT treatment balloon may be filled with a commonly used non-toxic radio-opaque contrast medium to verify integrity of the IRT treatment balloon. Once the integrity is verified, the contrast medium would be evacuated and shielded syringe 16 connected to the receptacle at the proximal end of the catheter shaft. Although the small amount of contrast medium that would remain in the IRT treatment balloon would dilute the radioactive liquid, the amount of dilution would be measurable and could be compensated.

Figure 2B:
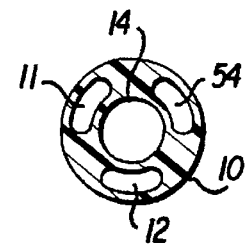
Figure 2C:
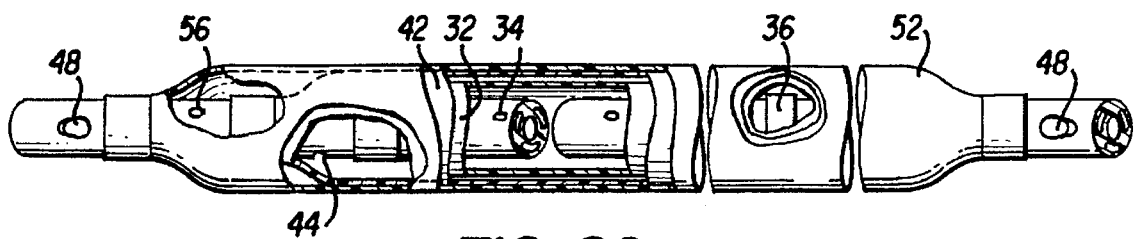

FIGS. 2A–2C illustrate an alternate embodiment of the present invention further including an outer containment balloon 52. Containment balloon 52 is an inelastic or preferably an elastic balloon, which is preferably made of latex or other medical grade material suitable for constructing puncture-resistant elastic balloons. Containment balloon 52 is attached at its proximal and distal ends to shaft 10 and completely surrounds treatment balloon 32. Containment balloon 52 is in communication with containment balloon inflation lumen 54 via containment balloon inflation lumen port 56, which in turn is in fluid communication with containment balloon luer fitting 58 at the proximal end of shaft 10.

In operation, after the IRT catheter is in position, but before IRT treatment balloon 42 is filled with the radioactive liquid, containment balloon 52 is filled with a commonly used non-toxic radio-opaque contrast medium injected through containment balloon luer fitting 58. The integrity of containment balloon is verified by fluoroscopy, pressure, or other suitable means and, if integrity is confirmed, the radio-opaque liquid is withdrawn and the procedure for injecting the radioactive liquid into treatment balloon 42 carried out. If the integrity of the containment balloon has been compromised (for example by sharp edges in guide catheters, guide wires, stents, etc.) a new catheter is selected and repositioned. By verifying integrity of the containment balloon after the balloon is in position, but before the radioactive liquid is injected, a substantial degree of safety against accidental injection of radioactive liquid into the patient's blood stream is achieved. Where a containment balloon is used (or blocking balloons as discussed with reference to FIGS. 3A–3C are used), pressure feedback device 22 may also be used to activate an emergency evacuation system. In the event the pressure feedback device detected a sudden drop in pressure (indicating rupture of the treatment balloon) the pressure feedback device would initiate an immediate withdrawal of all radioactive liquid from the patient, for example by opening a valve to a shielded vacuum accumulator 28.

Several important considerations must be balanced in the design of an apparatus for safely and effectively injecting a radioactive liquid into a patient to irradiate a blood vessel to prevent restenosis. Although $^{125}$I and $^{32}$P are both emitters of low penetrating radiation suitable for use according to the present invention, $^{32}$P is preferred because it has a half-life of only 14.3 days as compared with the 60 day half-life of $^{125}$I. A shorter half life renders $^{32}$P safer to use because, in the event of a catastrophic failure involving leakage of radioactive liquid into the patient's blood stream, for a given calculated dose rate, a shorter half life will result in a lesser total body dosage. $^{32}$P is also a relatively pure beta radiation emitter. $^{32}$P has been used in the treatment of chronic leukemia, where it is injected directly into a patient's blood stream. Accordingly, substantial medical knowledge exists as to the effects of $^{32}$P in the blood stream.

In the leukemia treatment, depending on the patient's weight, a suspended radiation source of about 6 to 15 millicuries of $^{32}$P is used. Accordingly, for maximum safety, the preferred suspended-isotope IRT catheter should also use a source of no more than 6 millicuries. Prior experiments have shown that a dose of about 1000 to 3500 rads delivered to the blood vessel wall from a gamma radiation source is effective to inhibit the smooth muscle cell hyperplasia that causes restenosis. For low penetration sources, such as beta radiation emitters, it is believed a dosage up to 5,000 rads may be tolerated. For a 6 millicurie $^{32}$P source to deliver such a dose to the surface of the blood vessel, the balloon must be in position for substantially in excess of one minute, thus necessitating the perfusion ports.

For example, it is estimated that the balloon will absorb approximately 15% of the radiation delivered by the radioactive liquid. Accordingly, to deliver 2000 rads to the blood vessel wall, 2350 rads must be delivered to the inner wall of the balloon. A typical treatment balloon comprises a cylindrical balloon having an internal diameter of 3 millimeters, a length of about 30 millimeters, and an interior volume of approximately 0.2 cubic centimeters. Accordingly, to limit the total source to no more than 6 millicuries, 0.2 cubic centimeters of a liquid having a source concentration of no more than 30 millicuries per cubic centimeter must be used. A 30 millicurie per cubic centimeter source, however, requires about 6 minutes to deliver 2350 rads to the interior of the 3 millimeter diameter treatment balloon and thus requires about 6 minutes to deliver 2000 rads to the interior wall of the blood vessel.

The larger the balloon, the lower the concentration of the radiation source in the liquid must be to maintain the safe limit of 6 millicuries. However, the lower the concentration, the lower the dose rate and the longer the balloon must remain inflated to deliver an effective dose to the blood vessel wall.

To reduce the volume of radioactive liquid that must be used, angioplasty balloon 32 may be left partially or substantially filled during the IRT treatment. Because the liquid near the center of a body of radioactive liquid does not contribute significantly to the radiation emitted from the surface of the body, by leaving the angioplasty balloon partially filled in the center of the IRT treatment balloon, a smaller volume of radioactive liquid can be used without significantly affecting the radiation delivered to the vessel wall. Without the angioplasty balloon acting as an inert filler, to avoid exceeding the 6 millicurie limit, the same size treatment balloon would require a larger volume of lower concentration radioactive liquid, with a commensurately lower dose rate and longer required treatment interval.

FIGS. 3A–3C illustrate an additional embodiment of the present invention incorporating blocking balloons 62. Blocking balloons 62 are inelastic or preferably elastic balloons, which are preferably made of latex or other medical grade material suitable for constructing puncture-resistant elastic balloons. Blocking balloons 62 are sealed to shaft 10 proximal and distal of treatment balloon 42 between perfusion ports 48, and are in fluid communication with a common blocking balloon inflation lumen 64 via blocking balloon inflation ports 66. Blocking balloon inflation lumen 64 is, in turn, in fluid communication with blocking balloon luer fitting 68 at the proximal end of shaft 10.

In operation, after the angioplasty procedure is completed, blocking balloons 62 are inflated in the blood vessel until the blood flow past the balloons is substantially stopped (the flow of blood in the vessel itself continues through the perfusion ports). The treatment balloon 42 is then inflated with the radioactive liquid for treatment of the blood vessel walls. In the event treatment balloon 42 ruptures and, where present, containment balloon 52 also fails, the radioactive liquid is still contained in the blood vessel between blocking balloons 62. The radioactive liquid can then be withdrawn either through any of the inflation lumens that, because of the breach, are in fluid communication with the interior of the blood vessel between the blocking balloons 62, or preferably withdrawn automatically using the emergency evacuation system discussed with reference to FIGS. 2A–2C. Blocking balloons may also be used in lieu of containment balloon 52, especially in particularly small lumens where a smaller profile is desirable.

FIGS. 4A–C illustrate an embodiment of the present invention for use in blood vessels that are too small to admit a catheter having a profile large enough to support independent inflation lumens for an angioplasty and an IRT balloon. The reduced-profile IRT catheter comprises shaft 10 having a single multi-purpose inflation lumen 81, a conventionally formed tip that seals the end of the inflation lumens, and may include longitudinal guidewire/injection/perfusion lumen 14 which passes through the tip.

FIG. 4C is an enlarged view of the distal end of the embodiment of the catheter. Angioplasty balloon 32 comprises a conventional elastic or preferably an inelastic balloon, which may preferably be made from polyethylene terephthalate (PET), polyvinyl chloride (PVC), or other medical grade material suitable for constructing a strong non-compliant balloon. Angioplasty balloon 32 is in fluid communication with multi-purpose inflation lumen 81 via ports 84. Preferably, angioplasty balloon 32 is surrounded by IRT containment membrane 92, which is sealed to catheter shaft 10.

In a preferred method of operation, after the distal end of the catheter is properly positioned in a stenosed region of the blood vessel, angioplasty balloon 32 is filled with a non-toxic fluid contrast medium injected through fitting 20 by means of an injector that mates with, but is detachable from fitting 20. The fluid is injected until angioplasty balloon 32 expands the stenosed region to an appropriate size. The fluid is then evacuated and, preferably, inflation lumen 81 exposed to a vacuum to remove as much of the fluid contrast medium as possible. Balloon 32 is then filled with radioactive liquid 30 until the walls of the balloon engage the walls of the blood vessel. The balloon is maintained in this inflated state for a predetermined period of time calculated to deliver an effective dose of radiation to the wall of the blood vessel. The radioactive liquid is then withdrawn from the balloon and the catheter withdrawn from the patient's body. A small amount of contrast medium will remain in balloon 30 after the angioplasty procedure to dilute the radioactive liquid. However, the dilution may be compensated, by increasing the initial concentration of the radioactive liquid or, preferably by increasing the treatment interval. The containment membrane 92 contains the radioactive liquid in the event the angioplasty balloon ruptures when filled with the radioactive liquid.

Thus, the present invention provides safe and effective method and apparatus for combining angioplasty and restenosis prevention into a single apparatus capable of relieving angioplasty and delivering an easily controllable inherently uniform dosage of radiation to control restenosis in the region of the blood vessel traumatized by the angioplasty procedure.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. An apparatus for localized intravascular radiotherapy of a blood vessel, such as a coronary artery, comprising:

a catheter, said catheter comprising an elongate member having a proximal and a distal end, said elongate member being sized and of sufficient flexibility to be introducible into a patient's body through a cardiovascular lumen until the distal end is disposed at a target area within the blood vessel, said elongate member further including first and second longitudinal holes therethrough defining an angioplasty balloon inflation lumen and an IRT treatment balloon inflation lumen;

an angioplasty balloon, said angioplasty balloon having an interior chamber, said angioplasty balloon being secured to the distal end of said elongate member with said interior chamber in fluid communication with said angioplasty balloon inflation lumen;

an IRT treatment balloon, said IRT treatment balloon comprising an inflatable balloon having an interior chamber, said IRT treatment balloon being secured to the distal end of said elongate member with said interior chamber surrounding said angioplasty balloon; and means for introducing a liquid containing a radioactive material into said IRT treatment balloon inflation lumen to fill the interior chamber of said treatment balloon for exposure of said target area to said radioactive material.

2. The apparatus of claim 1 further including means for perfusion of blood past said IRT treatment balloon when said balloon is expanded.

3. The apparatus of claim 1 further including means for detecting pressure in said IRT treatment balloon.

4. The apparatus of claim 1 further including a liquid containing a radioactive material, said liquid being introducible into said balloon by said introducing means.

5. The apparatus of claim 4 wherein said liquid containing a radioactive material comprises a liquid containing a material chosen from the group consisting of iodine and phosphorous.

6. The apparatus of claim 1 wherein said introducing means comprises a shielded syringe.

7. The apparatus of claim 6 wherein said shielded syringe is permanently attached to said catheter.

8. The apparatus of claim 7 wherein said shielded syringe further includes a fail-safe non-detachable fluid coupling and said catheter includes a corresponding fail-safe non-detachable receptacle.

9. The apparatus of claim 1 wherein said introducing means comprises a pump.

10. The apparatus of claim 9 wherein said pump is permanently attached to said catheter.

11. The apparatus of claim 10 wherein said pump further includes a fail-safe non-detachable fluid coupling and said catheter includes a corresponding fail-safe non-detachable receptacle.

12. The apparatus of claim 1 further including means for introducing a contrast medium into said IRT treatment balloon inflation lumen to fill the interior chamber of said IRT treatment balloon for verifying integrity of said IRT treatment balloon.

13. The apparatus of claim 1 further including a containment balloon, said containment balloon comprising an inflatable balloon having an interior chamber, said containment balloon being secured to the distal end of said elongate member with said interior chamber surrounding said IRT treatment balloon.

14. The apparatus of claim 12 wherein said elongate member further includes a longitudinal hole therethrough defining a containment balloon inflation lumen, the interior chamber of said comment balloon being in fluid communication with said containment balloon inflation lumen.

15. The apparatus of claim 13 further including means for introducing a contrast medium into said containment balloon inflation lumen to fill the interior chamber of said containment balloon for verifying integrity of said containment balloon.

16. The apparatus of claim 13 further including means for perfusion of blood past said containment balloon when said containment balloon is expanded.

17. The apparatus of claim 1 further including a first and second blocking balloon each having an interior chamber, said first blocking balloon being secured to the distal end of said elongate member distal of said treatment balloon, said second blocking balloon being secured to the distal end of said elongate member proximal of said treatment balloon; and wherein said elongate member further includes a blocking balloon inflation lumen, said blocking balloon inflation lumen comprising a longitudinal hole through said elongate member, the interior chambers of said first and second blocking balloons being in fluid communication with said blocking balloon inflation lumen.

18. An apparatus for localized intravascular radiotherapy of a blood vessel comprising:

a catheter, said catheter comprising a flexible elongate member having a proximal end and a distal end, said elongate member being sized and of sufficient flexibility to be introducible into a patient's body through a cardiovascular lumen until the distal end is disposed at a target area within the blood vessel, said elongate member further including a hole extending longitudinally therethrough from substantially the proximal end thereof defining an inflation lumen;

a balloon having an interior chamber, said balloon being secured to the distal end of said elongate member with said interior chamber in fluid communication with said inflation lumen;

a containment membrane surrounding said balloon to retain fluid leaking from said balloon in the event of rupture thereof; and means for introducing a fluid containing a radioactive material into said inflation lumen to fill the interior chamber of said balloon for exposure of said target area to said radioactive material, and for withdrawing said fluid after an effective dose of radiation has been delivered to the blood vessel wall in said target area.

19. A method of relieving a stenosis and preventing restenosis of a selected portion of a blood vessel in a patient comprising the steps of:

selecting a catheter comprising a flexible elongate member having a proximal end and a distal end, said catheter including an angioplasty balloon and an intravascular radiotherapy (IRT) treatment balloon secured to said distal end, said IRT treatment balloon comprising an inflatable balloon substantially surrounding said angioplasty balloon, said catheter being sized and of sufficient flexibility for introduction into the selected portion of the blood vessel;

advancing said catheter along a cardiovascular lumen of the patient until said IRT treatment balloon is disposed in the selected portion of the blood vessel;

inflating said angioplasty balloon through a first lumen in said catheter having an opening adjacent the proximal end thereof and communicating with said angioplasty balloon, sufficiently to relieve a stenosed region of said blood vessel;

at least partially deflating said angioplasty balloon through said first lumen in the catheter after relieving said stenosed region;

inflating said IRT treatment balloon with a liquid containing a radioactive material through a second lumen in said catheter having an opening adjacent the proximal end thereof and communicating with said IRT treatment balloon;

maintaining said IRT treatment balloon inflated with said liquid for a predetermined period of time sufficient to deliver an effective dose of radiation to the blood vessel wall in the selected portion of the blood vessel;

withdrawing said liquid from said IRT treatment balloon through said second lumen in the catheter immediately after said predetermined period of time has elapsed to allow said IRT treatment balloon to collapse, and substantially fully deflating said angioplasty balloon if only partially deflated previously; and withdrawing said catheter from the patient.

20. The method of claim 19 wherein said IRT treatment balloon extends longitudinally along the catheter at least slightly beyond the ends of said angioplasty balloon so that when said IRT treatment balloon is inflated with said liquid containing a radioactive material, radiation is delivered to an extended portion of the blood vessel wall relative to that occupied by the length of the angioplasty balloon in the selected portion of the blood vessel.

21. The method of claim 19 wherein said catheter further includes a containment balloon disposed about said IRT treatment balloon, and further including the step of:

inflating said containment balloon with a radio-opaque contrast medium to verify integrity of said containment balloon prior to inflating said IRT treatment balloon.

22. A method of relieving a stenosis and preventing restenosis of a selected portion of a blood vessel in a patient comprising:

selecting a catheter comprising a flexible elongate member having a distal end with a balloon secured adjacent the distal end and a flexible containment membrane surrounding said balloon to prevent leakage through the balloon from entering the blood vessel, said catheter being sized and of sufficient flexibility for introduction into the selected portion of the blood vessel;

advancing said catheter along a vascular lumen of the patient until said balloon is disposed in the selected portion of the blood vessel;

inflating said balloon with fluid to compress a stenosed region of the blood vessel wall along said selected portion of said blood vessel;

withdrawing said fluid from said balloon and, while maintaining the balloon substantially in place along the selected portion of the blood vessel, inflating said balloon with a radioactive liquid;

maintaining said balloon inflated with said radioactive liquid for a predetermined period of time sufficient to deliver an effective dose of radiation to the blood vessel wall in the selected portion of the blood vessel;

withdrawing said radioactive liquid from said balloon immediately after said predetermined period of time has elapsed to cease irradiation of the blood vessel wall and to allow said balloon to collapse;

preventing the radioactive liquid from entering the blood vessel by containing any liquid that leaks through the balloon within the containment membrane; and thereafter withdrawing said catheter from the patient.

* * * * *